United States Patent [19]

Scholl et al.

[11] Patent Number: 4,990,339

[45] Date of Patent: Feb. 5, 1991

[54] DERMAL TREATMENT FILM

[75] Inventors: Steven L. Scholl, Cottage Grove; Eugene R. Simmons, Maplewood; William L. Bunnelle, Hugo, all of Minn.

[73] Assignee: H. B. Fuller Company, St. Paul, Minn.

[21] Appl. No.: 124,257

[22] Filed: Nov. 16, 1987

[51] Int. Cl.$^5$ .................... A61L 15/24; A61K 7/40; A61F 13/00

[52] U.S. Cl. ..................... 424/443; 523/105; 523/111; 128/113.1; 128/114.1; 128/156; 424/447; 424/448; 106/162; 524/27; 524/612

[58] Field of Search ............. 536/20; 424/443, 447, 424/448; 523/105, 111; 128/113.1, 114.1, 156; 524/27, 612; 106/162

[56] References Cited

U.S. PATENT DOCUMENTS

| | | | |
|---|---|---|---|
| 2,579,367 | 12/1951 | Curtis et al. | 424/447 |
| 2,824,559 | 2/1958 | Sullivan | 424/447 |
| 2,835,639 | 5/1958 | Widmer et al. | 524/46 |
| 2,835,641 | 5/1958 | Widmer et al. | 524/101 |
| 3,241,553 | 3/1966 | Steiger | 128/156 |
| 3,293,245 | 12/1966 | Litt et al. | 524/104 |
| 3,328,259 | 6/1967 | Anderson | 424/445 |
| 3,339,546 | 9/1967 | Chen | 604/304 |
| 3,483,151 | 12/1969 | Biarnais et al. | 525/7 |
| 3,565,247 | 2/1971 | Brochman | 521/91 |
| 3,579,630 | 5/1971 | Herz et al. | 424/47 |
| 3,932,358 | 1/1976 | de Cleur et al. | 528/288 |
| 3,950,578 | 4/1976 | Laumann | 427/378 |
| 3,966,836 | 6/1976 | de Cleur et al. | 525/438 |
| 3,969,498 | 7/1976 | Catania et al. | 424/445 |
| 3,972,328 | 8/1976 | Chen | 128/156 |
| 4,001,068 | 1/1977 | Robinson et al. | 156/315 |
| 4,113,851 | 9/1978 | Leveen et al. | 424/447 |
| 4,137,385 | 1/1979 | Reitz et al. | 525/375 |
| 4,143,100 | 3/1979 | Schulz et al. | 525/353 |
| 4,144,211 | 3/1979 | Chamberlin et al. | 524/612 |
| 4,163,718 | 8/1979 | Chamberlin et al. | 210/735 |
| 4,186,191 | 1/1980 | Chamberlin et al. | 424/78 |
| 4,226,746 | 10/1980 | Schulz et al. | 525/340 |
| 4,226,956 | 10/1980 | Schulz et al. | 525/331.3 |
| 4,326,532 | 4/1982 | Hammar | 604/266 |
| 4,391,799 | 7/1983 | Mason, Jr. et al. | 424/619 |
| 4,393,048 | 7/1983 | Mason, Jr. et al. | 424/619 |
| 4,408,001 | 10/1983 | Ginter et al. | 524/376 |
| 4,421,583 | 12/1983 | Aldred et al. | 156/167 |
| 4,436,789 | 3/1984 | Davis et al. | 428/537.5 |
| 4,436,867 | 3/1984 | Pomplun et al. | 524/503 |
| 4,464,438 | 8/1984 | Lu | 428/516 |
| 4,466,431 | 8/1984 | Tharrat et al. | 128/156 |
| 4,474,928 | 10/1984 | Hoenig et al. | 428/480 |
| 4,481,167 | 11/1984 | Ginter et al. | 422/29 |
| 4,485,220 | 11/1984 | Hefner, Jr. et al. | 525/411 |
| 4,522,967 | 6/1985 | Sheldon et al. | 525/186 |
| 4,524,064 | 6/1985 | Nambu | 424/81 |
| 4,528,044 | 7/1985 | Warchol | 528/402 |
| 4,551,490 | 11/1985 | Doyle et al. | 524/22 |
| 4,562,225 | 12/1985 | Huber et al. | 524/602 |
| 4,570,629 | 2/1986 | Widra | 128/156 |
| 4,599,209 | 7/1986 | Dautzenberg et al. | 264/7 |
| 4,623,688 | 11/1986 | Flanagan | 524/377 |
| 4,678,833 | 7/1987 | McCreedy et al. | 525/186 |
| 4,695,465 | 9/1987 | Kigasawa et al. | 424/447 |

FOREIGN PATENT DOCUMENTS

| | | |
|---|---|---|
| 1179913 | 12/1874 | Canada . |
| 1180622 | 1/1985 | Canada . |
| 0138385 | of 0000 | European Pat. Off. . |

*Primary Examiner*—Ronald W. Griffin
*Attorney, Agent, or Firm*—Merchant, Gould, Smith, Edell, Welter & Schmidt

[57] ABSTRACT

A water soluble dermal treatment film for dressing burns, surface wounds, cuts, scrapes, rashes or other dermal wound or lesion comprises a flexible sheet-like dressing made of polyalkyloxazoline. The dressing can have a structural layer and a pressure sensitive adhesive layer. The structural layer can be made of a polyalkyloxazoline composition formulated to obtain a flexible structural sheet. The pressure sensitive adhesive layer can be formulated to obtain pressure sensitive properties, maintaining the treatment film in position during its use. At such time the treatment film is to be removed, it can be removed without harsh scrubbing methods with a warm aqueous spray or soak. The sheet-like treatment means can be reinforced or impregnated with medicinal compositions to induce healing, reduce infection or stabilize the skin surface.

31 Claims, No Drawings

DERMAL TREATMENT FILM

FIELD OF THE INVENTION

The invention relates to a polymeric material in a film or sheet-like format that can be applied to a mammalian or human surface as a dressing. Preferably, the sheet-like material can be applied to human skin in various formats for treatment of disease, rashes, wounds, lesions or other dermal malady.

BACKGROUND OF THE INVENTION

A great deal of attention has been directed to developing sheet-like dressings, for the treatment of body surfaces, using a variety of materials. Curtis et al, U.S. Pat. No. 2,579,367 teaches using a coagulated proteinaceous solution or paste, and forming a soluble, semipermeable, artificial bandage. Anderson, U.S. Pat. No. 3,328,259 teaches a film prepared from a cellulose derivative such as sodium carboxymethyl cellulose, glycerol, and water. The cellulose derivative is described as a composition that will cause the coagulation of blood plasma. Catania et al, U.S. Pat. No. 3,969,498 teaches a flexible wound dressing formed primarily from a water soluble dextran polymer. Mason, Jr. et al, U.S. Pat. Nos. 4,391,799 and 4,393,048 teach a protective gel composition for treating white phosphorous burn wounds containing water soluble hydrogels of alkali metal alginate and glycerine. Murray, Canadian Pat. No. 1,180,622 teaches forming a laminate comprising two sheets of a water soluble material having a layer of a mendicament.

In the treatment of dermal lesions, significant problems can arise in contacting lesions with treatments in general and with sheet-like dressings in particular. The application of a dressing can often disturb injured tissues. Portions of dressings can often be included in the formation of new skin during the healing of abrasions, cuts, and other skin injury. The removal of many dressings can cause significant pain and often can re-open at least portions of partially healed wounds. More particularly, in the treatment of other wounds such as burns and other more serious injuries or surface lesions that involve a significant area of the skin, simply applying many available sheet-like dressings to the wound can cause severe pain and discomfort. Further, the removal of such dressings after a period of a few days can cause additional pain and suffering. Further, sheet-like dressings need to be formulated such that the dressings can include antibiotic compositions, compositions that can promote wound healing, pain killers, and other treatment agents.

Accordingly, a substantial need exists for dressings that can be applied and removed from the skin surface with minimal pain and discomfort while at the same time providing a vehicle for the application of beneficial treatments to the skin surface.

BRIEF DISCUSSION OF THE INVENTION

The invention resides in a dermal treatment film that can be easily applied in a sheet-like form or cast-in-place form, a cooled extruded hot melt or a liquid concentrate and can be easily removed with an aqueous agent including cool water, warm water, a detergent containing aqueous solution, and other mild aqueous cleaning or treatment agents.

The dermal treatment film can be formed into a structurally stable sheet-like material. In a preferred format, the dressing can have a pressure sensitive adhesive (PSA) layer in conjunction with a structural layer. The structural layer can comprise a non-tacky layer. The pressure sensitive adhesive layer can comprise 10-75 wt. % of a polyalkyloxazoline polymer, 10-75wt. % of a functional diluent comprising a hydroxy compound or a carboxylic acid compound, and 5-50 wt. % of a tackifier compatible with the pressure sensitive adhesive formulation.

The nontacky layer can comprise a natural or synthetic fiber, fabric or tape adhered to the wound and skin surface using the adhesive of the invention. Commonly available fibers, fabrics and tapes can be used in this aspect of the invention including woven and nonwoven fabrics made from cotton, rayon, synthetic polymers, tapes made from polymer and cellulosic films, nonwoven fibers made from fiberglass, cotton, polypropylene, and other sources. The structural layer can also comprise a nontacky layer prepared from the polyalkyloxazoline polymer of the invention.

The polyalkyloxazoline structural layer can contain a broad array additional ingredients that can aid in adhesion to the skin surface, can enhance the structural stability of the film, or can promote wound treatment or skin stability including agents such as antibiotics, antiseptics, analgesics, fibers, a woven or nonwoven mesh, dyes, solvents, curing agents, or other functional compounds.

The dermal treatment in the form of a film extruded from a hot melt, can have a release liner covering a PSA (pressure sensitive adhesive) layer, and can be applied to the skin by removing the release liner and applying the dermal treatment PSA layer to a wound or other lesion on the skin. Alternatively, the dermal treatment can be formed by casting the pressure sensitive adhesive layer and the polyalkyloxazoline structural layer in situ on a wound site or from an aqueous or other solvent based system of the composition. The materials can be sprayed on, brushed on or coated in an immersion step.

At such time as the dressing needs to be replaced or removed, the treatment film can be completely dissolved in an aqueous bath and removed from the wound site in the absence of any mechanical contact. Alternatively, if the sensitivity of the wound and the surrounding skin is minimal, the removal of the film can be aided using mild scrubbing action with warm water or aqueous cleaners.

DETAILED DISCUSSION OF THE INVENTION

The dermal treatment film of this invention is a sheet-like polymeric material that can be applied to the skin in a variety of formats for the purpose of treating the skin surface. The polymeric materials that make up the dermal film comprise conventional material and synthetic fiber fabrics and films in conjunction with polyalkyloxazoline polymer which can aid in maintaining structural integrity, bond strength to the skin, or aid in the treatment of the skin surface.

The sheet-like dermal treatment film of the invention can contain antimicrobial agents that can be dissolved or suspended in the polymer material or blend thereof. Antimicrobial agents when included in the film treatment means of the invention are typically mixed into a hot melt or in an aqueous solution that can contain a thickener if required which is then added to the polymer base during the manufacture of the sheet-like treatment layers. Antimicrobial agents that can be used in the invention are well known dermal treatment agents including, for example, sulfadiazine, silver sulfadiazine, benzalkonium chloride, cetalkonium chloride, methylbenzethonium, neomycin sulfate, hexachlorophene, eosin, penicillin G, cephalothin, cephaloridine, tetracycline, linkomycin, nystatin, kanamycin, penicillinase-resistant penicillins, fradiomycin sulfate, and other well known antimicrobial agents. If the antimicrobial agent is not sufficiently water soluble, the antimicrobial can be introduced into the polymer material of the invention by adding the antimicrobial in a powder form or carried on a powder support. The antimicrobial, which can be diluted by carriers, can be added to the surface of the sheet-like material during formation, to the polymer blend or can be added in combination with other film components.

The amount of antimicrobial agent added to the treatment material should be sufficient to provide an effective antimicrobial concentration or dose rate of the material to the skin surface. Typical concentrations of standard antimicrobials range from about 0.01 to 5% by weight of the antimicrobial in the film treatment.

For structural and wound treatment purposes, the film treatment of the material can contain either natural or synthetic fibers. The fibers can be woven or nonwoven and can be randomly or uniformly distributed throughout the polymer material. The fibers can be of minimal length, about 1 millimeter or greater, or can, in a woven or nonwoven fabric format, have a length equal to or greater than the dimensions of the polymeric film material of the invention. Fibers that can be included in the film treatment of the invention include rayon, nylon, cellulose acetate, modified proteins, polyesters, polyacrylics, polyethylene, polypropylene, glass fibers, polyvinyl alcohol polymers, and others. Natural fibers that can be used include fibers from both animal or plant sources. Examples of natural plant fibers include cotton, flax, hemp, jute, linen and other well known fibers.

A preferred ingredient for the films of the invention comprises chitin. Chitin is a naturally occurring aminopolysaccharide occurring as a structural material, internal or external skeleton in the shells of mollusks such as squid, lobsters, crabs and other marine invertebrates Chitin can be obtained from the structural body members of these organisms in relatively pure form and can be made into a powder, a fiber, a sheet, or other functional form. Chitin has the unique ability to promote healing of surface lesions. Accordingly, chitin can be incorporated into the treatment films of this invention as a powdered or granular filler, randomly distributed fiber, a woven or nonwoven fabric, or as a film support.

During manufacture such fibers can be incorporated into the sheet-like materials of the invention in a variety of formats. The fibers can be in the form of a woven fabric, a nonwoven fabric or can be randomly distributed throughout the treating material. During manufacture the fibers can be incorporated by casting the polymeric materials onto or around a woven or nonwoven fabric from a solvent source, extruding the fabric with the polymeric material, spraying the polymeric material onto the fabric, or other well known conventional manufacturing techniques. Additionally, random fibers can be added to the material during manufacture, can be blended and can be extruded as a component of the polymeric material.

Virtually any skin problem requiring treatment by an active surfactant or protection from the effect of sunlight, dirt, water or other environmental hazard, can be treated using the dermal film treatment of the invention. Such problems include dermatitis, puncture wounds, abrasions, cuts, eczema, pimples, blackheads, poison oak and poison ivy contact dermatitis, etc. Wounds referred to in the invention are open wounds caused by the injury of living tissues through a mechanical insult or through surgical operation. An incision caused by scalpel or a knife, stab wound, needle market or pocket knife wound or crushing wounds such as stretching, elongation, etc. can be treated. Additionally, burns caused by fire, chemical hazard, electric shock, radiation (X-ray, gamma ray, microwave or other photon-based energy, beta ($e^-$) particle, alpha particle, proton, or other ionizing radiation) or other energy source can be treated using the compositions of the invention. Skin infections including infected wounds, skin abscesses, boils, leprosy, etc. can also be treated.

The sheet-like treatments of the invention can be produced in a variety of formats. The size of the film can vary from small (an area of about 0.5 to 1 $cm^2$) that can be applied to small puncture wounds or other dermal problem). Alternatively, the sheet-like substrate can be long, thin sheets of material that can be used to wrap fingers, arms, legs, torso, or head wounds with a single or multiple layer of the material having an area of about 1 $cm^2$ to $m^2$. Alternatively, the material can come in the form of large (about 1 to 10 $m^2$ or more) sheets that can be applied to larger skin surface areas such as torso, upper thigh, gluteal region, or can be cut into smaller shapes for the purpose of treating irregular shaped burns, abrasions, chemical burns, or other lesions.

The treatment films of the invention can vary in thickness depending on the number of layers and the compositions used in forming the treatment film. A single layer non-adhesive film can be from 0.01 to 1 millimeters, preferably 0.02–0.5 millimeters, in thickness in order to provide minimal structural integrity. Bi-layer structural treatment films having a structural layer and a pressure sensitive adhesive layer with release liner can range from about 0.02 to 3 millimeters, preferably 0.03 to 2 millimeters, in thickness. Additional layers can add similar increments to the thickness dimension of the film.

Such sheet-like treatment films can be formed from a single layer of the polyethyloxazoline polymer that can include other ingredients. Alternatively, the polyethyloxazoline polymer sheet can have a coating of a pressure sensitive adhesive composition. The pressure sensitive adhesive layer can be formed by introducing into the polyethyloxazoline polymer sufficient tackifier and other ingredients to create a pressure sensitive adhesive layer in the film treatment itself. Alternatively, the structural layer can be coextruded or cast in conjunction with a tackified polyethyloxazoline layer which adheres and can be applied to dermal wounds.

The pressure sensitive adhesive layer on the treatment film can be covered with a release liner that protects the adhesive nature or tackiness of the adhesive layer until the release liner is removed just prior to adhesion to the dermal surface.

As currently envisioned, the treatment film of the invention can be manufactured and applied to a treatment site in one of two preferred modes. First, the treatment film can be formed using hot melt extrusion technology, packaged, distributed and sold as an adherent treatment. Secondly, the treatment film can be formed in situ on a sensitive dermal lesion by applying the material in a liquid form which will solidify over time.

The polymeric polyalkyloxazoline polymer compositions of this invention are typically manufactured by heating in an appropriate formulation vessel the tackifier or plasticizer portion of the invention in conjunction with the optional inorganic filler or other diluent portion. Such components are heated in a stainless steel vessel until melted and into the melt is added under conditions of high shear the polyalkyloxazoline polymer. The polymer should be added to the melt at a rate such that it is readily and smoothly incorporated into the melt mixture. After the polymer has been added, additional materials including other polymeric materials, antimicrobials, fibers, etc. can be added under appropriate conditions.

The following Table contains a formulation for the preferred composition of the treatment film of the invention having a structural layer and a pressure sensitive adhesive layer.

TABLE 1

| | Preferred Polymeric Constituents | | | |
|---|---|---|---|---|
| | Structural Layer | | PSA Layer | |
| | Useful | Preferred | Useful | Preferred |
| PeOx | 5-85 | 10-50 | 5-75 | 10-40 |
| Tackifier | 0-30 | 0-25 | 1-35 | 2-30 |
| Plasticizer | 5-60 | 20-50 | 5-60 | 10-50 |
| Fiber | 0-60 | 1-50 | 0-60 | 1-50 |
| Antimicrobial | 0-10 | 0.01-5 | 0-10 | 0.01-5 |
| Thermoplastic polymer | 0-25 | 0.1-25 | 0-25 | 0.1-25 |

The polyalkyleneimines (polyalkyloxazolines) which can be used in the adhesives of this invention are commonly prepared by the polymerization of heterocyclic monomers of the general formula I:

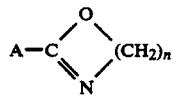

wherein A is a $C_{1-15}$ alkyl and n is 100–10,000. The polymers and polymerization techniques are in general as disclosed in U.S. Pat. Nos. 3,483,151 and 3,293,245, the disclosures of which are incorporated by reference herein.

Preferred polyalkyleneimines (polyalkyloxazolines) include N-substituted polyethyleneimines and polypropyleneimines which are prepared by polymerizing heterocyclic monomers of the formula I wherein n is 2 or 3. These polyalkyleneimines can be represented by the general formula II:

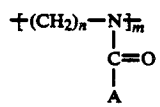

wherein A is as defined hereinabove, n is about 2–3 and m is about 50–100,000, preferably 100–7,500.

The molecular weights of the polymers derived from such monomers can range from less than 50,000 to 500,000 or above. The polymers are available in low (less than about 100,000), moderate (about 100,000 to 300,000) and high (greater than about 300,000) molecular weights. These polymers are soluble in water and many polar organic solvents, but can be advantageously insoluble in non-polar organic solvents. The polymers are thermally stable, low in solution viscosity, possess acceptable melt flow properties, and have acceptable human toxicity. The substituted polyalkyleneimine (polyoxazoline) polymers of this invention are available from the Dow Chemical Company.

The most preferred polyoxazoline polymers of this invention, for reasons of their low cost and high performance in adhesive applications, are polymers having the formula:

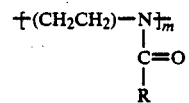

wherein m is as defined above and R is a $C_1$–$C_{12}$ alkyl such as methyl, ethyl, iso-propyl, t-butyl, cyclohexyl, cyclopentyl, methyl-cyclohexyl, dodecyl, and the like. Preferably, R will be an alkyl group having about 1–5 carbon atoms.

The polymer sheet-like compositions of this invention can contain a carboxylic acid functional compound having an acid number of at least 75. Both monomeric and polymeric acid functional compounds can be used to enhance a number of properties of the polymer base including homogeneity, viscosity, rate of set, solubility, heat resistance, and others. Monomeric compounds are typically small molecules having a molecular weight of less than about 1,000 having from 1 to 4 carboxylic acid groups. Examples of such carboxylic acid groups include $C_{6-24}$ fatty acids such as lauric acid, palmitic acid, oleic acid, stearic acid, linoleic acid, linolinic acid, aracadonic acid, and others. Other examples include the polyisobutylene and polypropylene substituted succinic acids, alkyl substituted benzoic acids, alkyl substituted phthalic acids, oxidized waxes, and others. Acid functional polymeric compounds could also be used in the adhesives of the invention. Such compositions include polymers having a molecular weight of about 500 and greater having an acid number of at least 75. Typical examples of such acid containing polymers include polymers containing repeating units of monomers such as acrylic acid, methacrylic acid, maleic anhydride, maleic acid, fumaric acid, vinyl benzoic acid, and other vinyl monomers containing at least one carboxylic acid functional group or carboxylic acid generating group such as an acid chloride or anhydride. Particular examples of such polymers include polyacrylic acid, polymethacrylic acid, ethylene acrylic acid copolymers, propylene methacrylic acid copolymers, styrene maleic anhydride copolymers, carboxylated vinyl acetate, carboxylated ethylene-styrene copolymers, carboxylated ethylene vinyl acetate copolymers, and others well known to the skilled chemist.

The sheet-like compositions of this invention can also contain a hydroxy substituted organic compound. The hydroxy substituted organic compound can be used to provide or enhance a number of properties of the composition. The hydroxy composition in combination with the other components of the invention can be used to form uniform homogeneous single phase compositions. Further, the hydroxy substituted organic compounds tend to produce polymeric blends with workable viscosity, controllable rate of set and heat resistance. If desired a sufficient quantity of a hydroxy substituted organic compound can substantially reduce or enhance pressure-sensitive adhesive (PSA) properties of the materials. For example, liquid compounds tend to enhance PSA properties while solids tend to reduce PSA properties. The hydroxy compositions can be essentially aliphatic or aromatic, small molecule or polymeric. Many hydroxy substituted organic compounds exist including alcohols, hydroxy substituted waxes, polyalkylene oxide polymers and copolymers such as CARBOWAX ® and many others. Preferred hydroxy substituted organic compounds include $C_{10-30}$ fatty acid alcohols, hydroxy substituted waxes, hydroxy substituted fatty acid mono-, di- and triglycerides, hydroxy substituted fatty acids, hydroxy substituted fats, hydroxy substituted fatty amides, diacetin, polyalkylene oxide polymers and copolymers made from polyethylene oxide, polypropylene oxide, and others. To ensure full compatibility, we have found that the hydroxyl number of the hydroxy substituted organic compound should be at least 150 and preferably between 200 and 500, and that at a level of more 20 wt-% or more of a 150 hydroxyl number hydroxy wax an effective amount, 5 to 10 wt-% of a $C_{8-20}$ fatty acid, preferably a $C_{8-20}$ saturated fatty acid can be used to ensure compatibility We believe that the acid can be omitted if the hydroxyl number of the hydroxyl compound is greater than 200.

Tackifying Agent or Resin

The polyoxazoline polymer itself can often have insufficient pressure-sensitive adhesive (PSA) properties for certain treatment purposes. The addition of a compatible tackifying resin is commonly made to form a sufficiently adherent pressure-sensitive polymer blend.

Many tackifying agents such as resins or resin blends are well known in the art. Such resins include rosin acids, hydrogenated rosins, tall oil pitch heads (residue), ACINTOL or UNITOL ® (Arizona Chemical), polyketones, polymerized mixed olefins, alkyl resins, phenolic resins, and terpene-phenolic resins. Especially preferred tackifying resins for use in the present compositions include the rosin acids (SYLVATAX ® , RX Silvachem Company), and terpene-phenolic resins such as the NIREZ ® series, e.g. NIREZ ® V-2040, V-2150 (Reichhold Chemicals, Inc., Pensacola, Fla.), having a hydroxy number of at least about 150.

Suitable rosin acids, having the appropriate acid number, include the FORAL ® AX acidic resin available from Hercules Inc. This resin is produced by hydrogenating wood rosin. Typical properties include a softening point of 75° C. by the Hercules drop method, a refractive index of 1.4960 at 100° C. and an abietic acid value of 0.15% (uv). The product typically has an acid number of about 150. Another preferred resin is the DYMEREX ® resin available from Hercules, Inc. This resin is composed predominantly of dimer acids derived from rosin, and includes lesser amounts of monomeric resin acids and neutral materials of rosin origin. Typical properties include a softening point of 150° C. by the Hercules drop method, a saponification number of 145, an average molecular weight of about 502, a density of about 1.069 kilograms per liter at 20° C., 8% unsaponifiable material, and an acid number of about 145. Another suitable tackifying resin is the STAYBELITE ® resin Hercules Inc.

Plasticizer

Plasticizers are generally classified as materials which can be incorporated into another material to increase its workability, flexibility, or distensibility. They can also enhance the tackifying effect of the tackifying resin. The addition of a plasticizer can lower melt viscosity, the temperature of the second order transition point or the elastic modulus of the treated material.

Commonly employed plasticizers include compounds of the following classes: adipic acid derivatives, azeleic acid derivatives, benzoic acid derivatives, diphenyl derivatives, citric acid derivatives, epoxides, glycolates, isophthalic acid derivatives, maleic acid derivatives, phosphorous acid derivatives, phthalic acid derivatives, polyesters, trimelitates, and the like. Castor oil, glyceryl trihydroxyoleate is available from a variety of chemical suppliers including CasChem, Inc. of New Jersey. CasChem provides this product as a variety of products having a Stokes viscosity of 7.5, specific gravity of 0.959, an iodine value of 86, a hydroxyl value of 164, a saponification value of 180, and a pour point of $-10°$ F.

Of the high acid plasticizers, especially suitable for use in the invention are a liquid hydroxylated fatty acid or a conjugated fatty acid, and isostearic acid. Isostearic acid is a commercially available material. One supplier is Emery Industries, Inc., of Cincinnati, Ohio. This product, sold under the mark EMERY 875-D, generally has an acid value of between 191.0 and 201.0, a free fatty acid value of 96–101%, a saponification value of 197–204, 3% unsaponifiable, an iodine value of no greater than 3, and a Titer of no greater than 9.0° C.

Other plasticizers can be selected from any of the commercially available benzoates, hydroxylated benzoates, or the acetates or benzoates of polyols, such as the acetates or benzoates of $C_2-C_6$ polyols comprising about 2–6 hydroxyl groups. Such plasticizers include acetin, glycerol tribenzoate (BENZOFLEX ® S-404), or pentaerythritol tetrabenzoate (BENZOFLEX ® S-552) or the mixed dibenzoates of dipropylene glycol and diethylene glycol (BENZOFLEX ® 50, Velsicol Corp., Chicago, Ill.). Another useful water insoluble plasticizer is butyl benzyl phthalate, available from Monsanto Co. as SANTICIZER ® 160.

Water soluble plasticizers are preferred for use in sheet-like treatment compositions which are formulated so as to be water releasable or soluble. Useful plasticizers of this type include the liquid polyalkylene glycols, e.g. polyethylene glycols (PEG) of molecular weights of about 200–800.

Wax

The hot melt adhesive compositions can also contain a wax. This component can aid in viscosity control and can reduce the tendency of the adhesive to block under conditions of high temperature, pressure or high humidity. The wax preferably has an acid number between about 50 and 300 or a hydroxy number of at least about 160. If the wax is a high acid material, more preferably the acid number will be between about 75 and 275, more preferably between about 85 and 200, or most preferably, between about 120 and 170. Lower acid number waxes (acid No. 575 or OHNOB150) can be incompatible with the polyalkyleneimine, and high acid number waxes can result in an adhesive which corrodes hot melt equipment. We have found that Hoechst "S" wax, a montan acid wax, is particularly suitable for use in this invention, for reasons of compatibility, melt point, viscosity control and rate of set. It is available from American Hoechst Corporation of New Jersey. This material has a melting point of from 80°–83° C., a congealing point of 76°–79° C., an acid value of 140–155, and a saponification value of 160–180. We have found that a hydroxyamide wax (Paracin 220) with an OH No. of 300 can be used.

Copolymer

The formulation may contain an ethylene-acid copolymer, to provide additional strength and toughness and increase the resistance to cold. It will have the same acid number as specified previously in connection with the wax component. A particularly suitable ethylene-acid copolymer is the ELVAX ® II ethylene copolymer resin available from E. I. DuPont De Nemours & Co. This resin is an ethylene acrylic acid copolymer. The grade 5950 is especially suitable because of compatibility and toughness of the final film. Typical properties of the ELVAX ® II 5950 resin include an acid number of 90, melt index (G/10min) of 25, tensile strength measured at ASTM D 638-82 of 3,820 p.s.i., elongation, measured at ASTM D 638-82 of 480%, elastic (tensile) print modulus, ASTM D 638-82 of 25,000 p.s.i., flexural modulus, ASTM D 79—81, Meth. 1, Proc. A of 14,000 p.s.i., density at 23° C. of 940 kg/m$^3$, durometer hardness, Shore A-2 of 94, and softening point, ring and ball, 138° C. Other suitable materials to provide the increased strength, toughness, and resistance to cold flow include temperature board failure.

Filler

The present adhesive formulations can also comprise an effective amount of an inorganic extender or filler, such as calcium carbonate, zinc oxide, alumina, clays, titanium dioxide, talc, carbon black, and the like. For example, the film can be formulated to be moisture-sensitive and/or water soluble can comprise up to about 35 wt. % of a mineral extender which is preferably fatty acid-ester coated to increase its organophilicity. One commercially available filler of this type is the stearate-calcium carbonate compound OMYACARB ® UF-T (Omya, Inc., Proctor, Vt.). Another commercially available filler is MINSPAR, a finely ground feldspar available from Indusman.

The film compositions may also incorporate relatively small amounts of adjuvants such as UV absorbers, heat stabilizers, release agents, additional antiblocking agents and antioxidants. Typical antioxidants include the IRGANOX ® series (Ciba-Geigy) and the distearyl pentaerythritol diphosphate (WESTON ® 619, Borg-Warner Chemicals). When present, such adjuvants will commonly make up less than 5% by weight of the present adhesives.

Compatible polymers that can be included in the sheet-like compositions of the invention include rubbery polymers and copolymers, acid functional polymers having an acid number of at least about 100, hydroxy (—OH) functional polymers having a hydroxyl number of about 150 or greater, nitrilo functional polymers including, for example, acrylonitrile, and other compatible polymers. Such polymers include styrene acrylic acid copolymers, ethylene acrylic acid copolymers, styrene alyl alcohol copolymers, ethylene vinyl alcohol copolymers, ethylene hydroxyethyl acrylate copolymers, ethylene hydroxyethyl methacrylate copolymers, ethylene hydroxy propyl acrylate copolymers, styrene-acrylonitrile copolymers, styrene-butadiene-acrylonitrile copolymers, impact modified styrene acrylonitrile rubbers, hydrogenated nitrile rubbers, nitrile rubber wherein the nitrile polymer contains about 60 to 20 wt-% acrylonitrile; polyvinyl pyrrolidone, polyvinyl caprolactan, polyamides, made from piperazine or amine mixtures thereof; halogenated polymers, epichlorohydrin rubber, chlorinated polyolefin, vinyl chloride, vinyllidine chloride copolymers, and others.

The following Examples further explain the manner of manufacture and compositions of the treatment films of the invention and include a best mode.

EXAMPLE I

Treatment Film Prepared From Hot Melt

Into a heated reaction vessel containing a blade mixer was placed 30 parts of a tackifying resin comprising a tall oil fatty acid (FORAL AX), and 2 parts of a hindered phenolic antioxidant (IRGANOX 1076). The contents of the mixer were mixed and heated to a melt temperature of about 250° F. Into the melt was placed 30 parts of castor oil and 10 parts of feldspar filler. The material in the mixer is agitated until uniform and into the mixer is placed slowly 23 parts of a polyethyleneoxazoline polymer (500,000 molecular weight—PEOX). The contents of the mixer was agitated after addition was complete until uniform and into the uniform blend was added 5 parts of an ethylene acrylic acid copolymer having an acid number of about 80. The contents were agitated until uniform and the uniform blend was cast into a uniform layer having a thickness of about 5 mils. The layer was nontacky and had substantial cohesive strength.

EXAMPLE II

Structural Layer

Into a stainless steel reaction vessel heated to 350°-375° F. having a blade mixer was placed 25 parts of a tackifying resin (PICCOFYN T-125), 20 parts of castor oil. The components were mixed in the vessel under conditions of high shear until homogeneous for approximately 10 minutes. To the mixture was added 10 parts of a hydroxy wax (PARICIN 220) and 18 parts of feldspar (MINSPAR No. 7). The mixture was agitated under high shear until uniform at 350°-375° F. for 10 minutes. Into the uniform, homogeneous blend was slowly added 25 parts of a polyethyloxazoline polymer having a molecular weight of 500,000 (PEOX—500). During the step-wise addition, the mixture was agitated at high shear and after the addition was complete (15 minutes) the composition was agitated until homogeneous. To the homogeneous melt was added 2 parts of butyl zymate antioxidant. The material was capable of being extruded at elevated temperature, approximately 350°-375° F. into thin, 0.1-10 mil structural nontacky sheets.

EXAMPLE III

Pressure Sensitive Adhesive

In a heated stainless steel reaction vessel at 400° F., equipped with a stainless steel blade was added 66.8 grams of a tackifying resin (FORAL AX), 61.8 grams of castor oil, 3.4 grams of butyl zymate antioxidant. The blend was mixed at high shear for 20 minutes until homogeneous. Into the uniform melt was slowly added 44 grams of polyethyloxazoline polymer (PEOX—500,000 molecular weight). The melt was mixed at high shear until homogenous (approximately 120 minutes). Into the melt was slowly added 22.8 grams of a styrene-butadiene-styrene block copolymer (KRATON 1102) and the melt was mixed until homogeneous (about 40 minutes). Once uniform, 0.88 gram of a 1% aqueous acetic acid solution containing 0.4% of chitosan was slowly added to the melt. Mixing was maintained until uniform and into the uniform melt was added 0.32 gram of a tincture of iodine containing 2 wt. % iodine in a 47 volume-% aqueous alcohol solution.

EXAMPLE IV

PSA Layer

Example III was repeated except that 13 parts of a styrene-isoprene-styrene block copolymer (KRATON 1117) was substituted for the 13 parts of KRATON 1102.

EXAMPLE V

Example III was repeated except that the 35 parts of castor oil was omitted and 35 parts of an ethylene acrylic acid polymer having an acid number of 120 (AC-5120) was substituted for the castor oil.

EXAMPLE II AND VI-XII

The following Examples of Table 2 are prepared following the blending procedures shown in the above Examples. The table lists the properties of materials made for the invention using the polyethyloxazoline polymer and a variety of functional compounds in useful blends.

TABLE 2

| Ingredient | II | VI | VII | VIII | IX | X | XI | XII |
|---|---|---|---|---|---|---|---|---|
| PeOx (500,000 MW) | 23.0 | 25.0 | 25.0 | 23.0 | 30.0 | 10.0 | 25.0 | 20.0 |
| Rosin acid | 30.0 | 38.0 | 33.0 | 30.0 | 30.0 | 50.0 | | 40.0 |
| Antioxidant | 2.0 | 2.0 | 2.0 | 2.0 | 2.0 | 2.0 | 2.0 | |
| Castor oil | 30.0 | 35.0 | 35.0 | 35.0 | 30.0 | 38.0 | 20.0 | |
| Feldspar (filler) | 10.0 | | | | | | 18.0 | |
| EAC* (Acid No. = 80) | 5.0 | | 5.0 | | | | | |
| EAC* (Acid No. = 120) | | | | 10.0 | | | | |
| Dimer acid | | | | | 8.0 | | | |
| Phenol-modified terpene resin | | | | | | | 25.0 | |
| Hydroxystearamide wax | | | | | | | 10.0 | |
| Isostearic acid | | | | | | | | 30.0 |
| Ethylene-acrylic acid interpolymer (Acid No. = 90) | | | | | | | | 10.0 |
| 180° Peel (initial)/ln. in. | 3.5 lbs. | 3.5 lbs. | 3.5 lbs. | 3.5 lbs. | | | | 2.2 lbs. |
| 2.2 lbs. (24 hrs.)/ln. in. | 6.5 lbs. | 5.5 lbs. | 5.5 lbs. | 4.5 lbs. | | | | |
| Static Shear | 200 min. | 100 min. | 150 min. | 160 min. | | | | 40 min. |
| Loop tack | 26 oz. | 30 oz. | 30 oz. | 24 oz. | | | | 18 oz. |
| Polyken tack | 425 | 650 | 400 | 550 | | | | 458 g |
| Viscosity, 300° F. (cPs) | 8750 | 4500 | 6000 | 3250 | | | | |

*EAC = ethylene-acrylic acid copolymer.

EXAMPLE XIII 200 grams of the material of Example III was dissolved in an aqueous ammoniacal (pH 10) solution containing 20 grams of an acetylenic glycol surfactant blend in polypropylene glycol (SURFYNOL TG-E) in 250 grams of water. The material was mixed at 180° F. until a uniform suspension solution was formed. The solution (about 50 wt. % solids was sprayed on the skin surface resulting in an intact, tacky treatment film.

The Examples shown above in conjunction with data relating to the properties of the treatment film clearly demonstrates the utility of the films of this invention for the purpose of treating skin. It is apparent that the material can be made in a variety of formats, can be applied to the surface of the skin, and can have useful treatment properties.

The discussion, Examples and data found above provide a complete explanation of the current understanding of the invention. However, since many embodiments of the invention may be derived without department from the spirit and scope of the invention, the invention resides in the claims hereinafter appended.

We claim:

1. An aqueous soluble dermal treatment film which comprises:
    (a) a structural layer comprising a polyalkyloxazoline polymer; and
    (b) a pressure sensitive adhesive layer comprising 10–75 wt. % of a polyalkyloxazoline polymer, 10–75 wt. % of a functional diluent comprising a hydroxy compound or a carboxylic acid compound; and 5–35 wt. % of a compatible tackifier.

2. The film of claim 1 wherein the polyalkyloxazoline polymer is a compound of the formula:

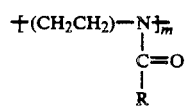

wherein R is a $C_{1-12}$ alkyl and n is about 50 to 100.000.

3. The film of claim 1 wherein the structural layer or the pressure sensitive adhesive layer additionally comprises an acrylic acid polymer.

4. The film of claim 3 wherein the acrylic acid polymer comprises an ethylene acrylic acid copolymer.

5. The film of claim 1 wherein the tackifier comprises a composition selected form the group consisting of a hydrogenated wood rosin, terpene-phenol resin and mixtures thereof.

6. The film of claim 1 wherein the pressure sensitive adhesive layer comprises 10–50 wt. % of a polyalkyloxazoline polymer, 10–30 wt. % of a hydroxy wax, and 15–35 wt. % of a tackifying agent.

7. The film of claim 1 wherein either the structural layer, the pressure sensitive adhesive layer or both additional comprise an antimicrobial composition.

8. The film of claim 1 wherein the structural layer additionally contains a fiber.

9. The film of claim 1 wherein additionally comprises a wound healing promoter.

10. The treatment film of claim 9 wherein the wound healing promoter comprises chitin, chitosan, derivatives thereof or mixtures thereof.

11. An aqueous soluble dermal treatment film which comprises:

(a) a structural layer comprising a polyalkyloxazoline polymer; and
(b) said layer containing a component selected from the group consisting of a fiber reinforcement, an antimicrobial, an analgesic, a wound healing promoter, or mixtures thereof.

12. The film of claim 11 wherein the polyalkyloxazoline polymer is a compound of the formula:

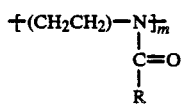

wherein R is a $C_{1-12}$ alkyl and n is about 50 to 100.000.

13. The film of claim 11 wherein the structural layer additionally comprises an acid functional compound, a hydroxy functional compound, or mixtures thereof.

14. The film of claim 11 wherein the film additionally comprises a tackifier.

15. The film of claim 11 wherein the treatment film additionally comprises a woven or nonwoven fabric.

16. The film of claim 11 wherein the treatment film additionally comprises a wound healing promoter.

17. The film of claim 16 wherein the wound healing promoter comprises chitin, chitosan, derivatives thereof, or mixtures thereof.

18. The film of claim 11 which comprises a pressure sensitive adhesive film.

19. The film of claim 11 which comprises a non-tacky film.

20. An aqueous liquid concentrate for application to the surface of skin to form a dermal treatment film removable by an aqueous treatment, which concentrate comprises:
(a) a major proportion of an aqueous liquid;
(b) about 5 to 85 wt. % of a polyoxazoline polymer to form a structural layer; and
(c) an effective amount of a compatible tackifier, plasticizer or mixtures thereof.

21. The aqueous concentrate of claim 20 wherein the polyalkyloxazoline polymer is a compound of the formula:

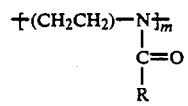

wherein R is a $C_{1-12}$ alkyl and n is about 50 to 100.000.

22. The aqueous concentrate of claim 20 wherein the tackifier comprises a composition selected from the group consisting of a hydrogenated wood rosin and a terpene-phenol resin.

23. The aqueous concentrate of claim 20 wherein the plasticizer comprises a composition selected from the group of castor oil, hydroxylated fatty acids or mixtures thereof.

24. The aqueous concentrate of claim 20 wherein the composition comprises about 10 to 75 wt. % of a polyalkyloxazoline polymer.

25. The aqueous concentrate of claim 20 wherein the composition additionally comprises an antimicrobial, an analgesic, a wound healing promoter, or mixtures thereof.

26. A method of treating a dermal lesion which comprises applying to the dermal surface an aqueous concentrate capable of forming a treatment film removable by an aqueous treatment which comprises:
(a) a major proportion of an aqueous liquid; and
(b) an effective concentration of a polyalkyloxazoline polymer to form a structural layer.

27. The method of claim 26 which additionally comprises applying the aqueous concentrate to a fiber applied to the dermal surface.

28. The method of claim 26 wherein the concentrate additionally comprises a compatible tackifier, a plasticizer or mixtures thereof.

29. The method of claim 26 wherein the polyalkyloxazoline polymer is a compound of the formula:

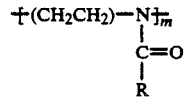

wherein R is a $C_{1-12}$ alkyl and n is about 50 to 100.000.

30. The method of claim 26 wherein the composition comprises about 10 to 75 wt. % of a polyalkyloxazoline polymer.

31. The method of claim 26 wherein the concentrate additionally comprises an antimicrobial, an analgesic, a wound healing promoter, or mixtures thereof.

* * * * *

UNITED STATES PATENT AND TRADEMARK OFFICE
CERTIFICATE OF CORRECTION

PATENT NO. : 4,990,339

DATED : Feb. 5, 1991

INVENTOR(S) : Scholl, et al.

It is certified that error appears in the above-identified patent and that said Letters Patent is hereby corrected as shown below:

At column 11, line 68, and Col. 12 line 1, please delete "department" and insert --departing--.

At column 12, line 21, please delete "100.00." and insert --100,000.--.

At column 12, line, 58 and 59, please delete "additional" and insert --additionally--.

At column 12, line 62, please delete "wherein" and insert --which--.

At column 13, line 18, please delete "100.000." and insert --100,000.--.

At column 14, line 7, please delete "100.000." and insert --100,000.--.

At column 14, line 44, please delete "100.000." and insert --100,000.--.

Signed and Sealed this

Eighteenth Day of August, 1992

Attest:

DOUGLAS B. COMER

*Attesting Officer*     *Acting Commissioner of Patents and Trademarks*